United States Patent
Clark et al.

(10) Patent No.: US 9,999,586 B2
(45) Date of Patent: Jun. 19, 2018

(54) SILICONE MODIFIED POLYOLEFINS IN PERSONAL CARE APPLICATIONS

(71) Applicants: Dow Global Technologies LLC, Midland, MI (US); Rohm and Haas Company, Philadelphia, PA (US)

(72) Inventors: Thomas P. Clark, Midland, MI (US); Vivek Kalihari, Midland, MI (US); Nahrain E. Kamber, Midland, MI (US); John W. Kramer, Midland, MI (US); Xiaodong Lu, North Wales, PA (US); Ying O'connor, Coatesville, PA (US); Thomas H. Peterson, Midland, MI (US); Curtis Schwartz, Ambler, PA (US); Qichun Wan, Midland, MI (US)

(73) Assignees: Dow Global Technologies LLC, Midland, MI (US); Rohm and Haas Company, Philadelphia, PA (US)

( * ) Notice: Subject to any disclaimer, the term of this patent is extended or adjusted under 35 U.S.C. 154(b) by 17 days.

(21) Appl. No.: 14/650,351

(22) PCT Filed: Nov. 22, 2013

(86) PCT No.: PCT/US2013/071404
§ 371 (c)(1),
(2) Date: Jun. 8, 2015

(87) PCT Pub. No.: WO2014/088839
PCT Pub. Date: Jun. 12, 2014

(65) Prior Publication Data
US 2015/0306018 A1     Oct. 29, 2015

Related U.S. Application Data

(60) Provisional application No. 61/734,509, filed on Dec. 7, 2012.

(51) Int. Cl.
*A61K 8/891* (2006.01)
*A61Q 19/00* (2006.01)
*A61K 8/892* (2006.01)
*A61K 8/898* (2006.01)

(52) U.S. Cl.
CPC .............. *A61K 8/891* (2013.01); *A61K 8/892* (2013.01); *A61K 8/898* (2013.01); *A61Q 19/00* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 4,446,283 A | 5/1984 | Doi et al. | |
| 4,834,972 A | 5/1989 | Chang | |
| 4,891,072 A | 1/1990 | Cooper | |
| 4,954,335 A | 9/1990 | Janchipraponvej | |
| 5,219,560 A | 6/1993 | Suzuki et al. | |
| 5,830,447 A | 11/1998 | Hutchins et al. | |
| 6,048,935 A | 4/2000 | Penfold et al. | |
| 6,451,747 B1 * | 9/2002 | Decoster | A61K 8/895 424/401 |
| 6,471,952 B1 * | 10/2002 | Dubief | A61K 8/731 424/501 |
| 6,531,142 B1 | 3/2003 | Rabe et al. | |
| 7,863,361 B2 | 1/2011 | Falk et al. | |
| 2008/0003249 A1 * | 1/2008 | Kaneda | A61K 8/06 424/401 |
| 2008/0167421 A1 | 7/2008 | Yalvac et al. | |
| 2009/0214455 A1 | 8/2009 | Blin et al. | |

FOREIGN PATENT DOCUMENTS

| | | |
|---|---|---|
| EP | 388582 A2 | 9/1990 |
| EP | 1557435 A1 | 7/2005 |
| JP | H06166613 A | 6/1994 |
| JP | 2008174571 A | 7/2008 |
| WO | 9809608 A2 | 3/1998 |
| WO | 2004/065430 A1 | 8/2004 |
| WO | 2011034836 A1 | 3/2011 |

OTHER PUBLICATIONS

Exxonmobil, Escorez 5637 Product Sheet, Obtained Online on Jan. 30, 2017.
Silane Coupling Agent, a Guide to Silane Solutions, Dow Corning Toray Co., Ltd., October 2008 [Retrieved on Oct. 13, 2017]. Retreived From the Internet <URL:http://www.dowcorning.co.jp/ja_jp/content/japan/japanproducts/z003_silane_coupling_agents.pdf> p. 15.

* cited by examiner

*Primary Examiner* — Melissa L Fisher
(74) *Attorney, Agent, or Firm* — Edward L. Brant

(57) ABSTRACT

The present invention provides personal care formulations containing silicone modified polyolefins and having improved sensory feel, as well as being non-tacky and easily spreadable. The present invention also provides a method for treating body surfaces such as skin, hair, nails, etc., by applying the aforesaid personal care formulations externally to such a surface. The present invention also provides a method for improving the sensory feel of personal care formulations by including one or more silicone modified polyolefins in the formulations.

3 Claims, 1 Drawing Sheet

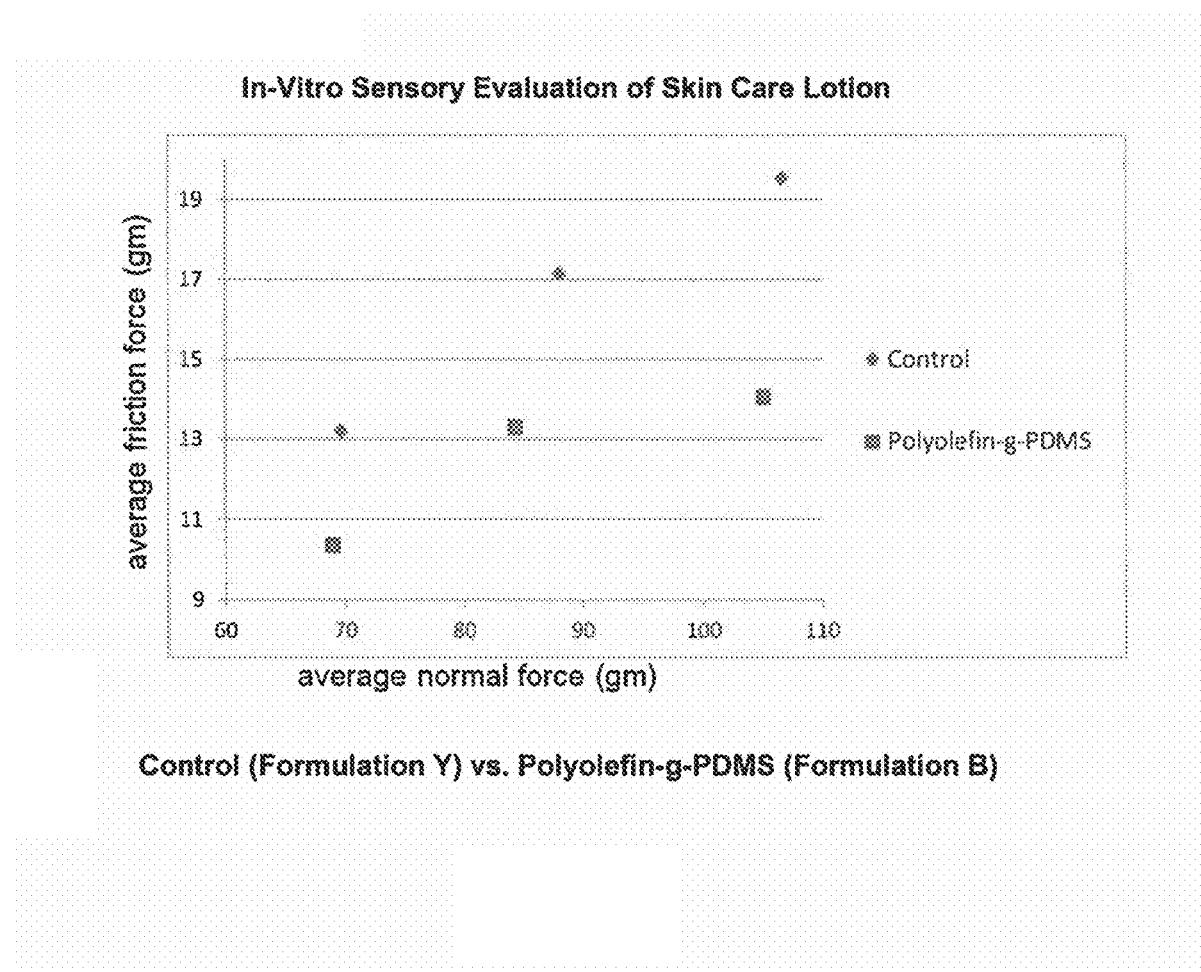

SILICONE MODIFIED POLYOLEFINS IN PERSONAL CARE APPLICATIONS

CROSS-REFERENCE TO RELATED APPLICATION(S)

This application claims priority to and is a 371 U.S.C. § 371 national phase application of International Application No. PCT/US13/071404, filed on Oct. 2, 2013, which claims the priority benefit of U.S. Provisional Application No. 61/734,509 filed on Dec. 7, 2012, each of which is incorporated herein by reference in its entirety

FIELD OF THE INVENTION

The present invention relates to personal care formulations containing silicone modified polyolefins and having improved sensory feel. The present invention also relates to methods for improving the sensory feel of personal care formulations by including silicone modified polyolefins in such formulations, as well as methods for treating skin, hair and nails by applying the aforesaid formulations thereto.

BACKGROUND OF THE INVENTION

Good sensory feel, i.e., softness and smoothness, is a necessity for both leave-on and rinse off types of personal care products, including face care products, body care products, hand care products, hair care products, sunscreens, antiperspirants, deodorants, color cosmetics, and face/hand/body wash. Many sensory enhancers have been developed to address this need, such as cationic surfactants (which are cationic compounds with quaternary ammonium functional groups, also known as "cationic quats") and silicone oils (which are typically polysiloxanes with organic side chains). Cationic quats and silicone oils are commonly used in skin care formulations to improve their sensory feel characteristics. However, high levels of cationic quats cause irritation on skin and silicone oils don't provide sufficient sensory benefits to satisfy consumer needs.

Silicone elastomers were developed as alternatives to cationic quats and silicone oils and are currently considered one of the best sensory modifiers used in skin care formulations. Due to the unique structure of silicone elastomers (i.e., loose-crosslinked silicone polymer swollen in silicone oil) and large particle size, it has a skin feel unlike any of the silicone fluids or cationic quats. Their feel has been described as "velvety", "powdery", "smooth," and "cushion feel". Also, their skin feel can be modified by controlling the amount of solvent in the formula, and therefore the degree of swelling. In general, the irregular shapes of these soft elastomer particles give a distinctly different feel on the skin.

The major drawbacks of silicone elastomers, however, are high cost and limited compatibility with other solvents. As a result, silicone elastomers tend to be limited high end skincare products, with the aforesaid shortcomings prohibiting their broad application for the mass market. There is also a contemporary trend toward reducing the use of silicones due to unwanted build-up on treated surfaces and environmental persistence. The absence of technology for producing new materials and formulations with performance comparable to silicone oils limits entry of new personal care products into high-volume and high demand personal care markets.

Nonetheless, efforts continue to develop alternatives to the silicone elastomers for achieving soft feel in personal care products. For example, U.S. Pat. No. 6,471,952 discloses cosmetic and dermatological compositions for treating keratinous material (i.e., hair) comprising at least one grafted silicone polymer and at least one combination of an anioinic polymer and a cationic polymer. The grafted silicone polymer contains a polysiloxane portion and a non-silicone organic chain portion, wherein either may be the main chain with the other grafted thereon. The polysiloxane portion may, for example, be derived from vinyl silicone macromers or polymers, and the non-silicone organic chain may, for example, be derived from monomers having at least one ethylenic unsaturation, such as acrylic acid, methacrylaic acid, N,N-dimethylacrylamide, maleic acid, maleic anhydride, hydroxyalkyl acrylates, hydroxyalkyl methacrylates, vinylpyrrolidone, acrylic or methacrylic acid esters of $C_1$-$C_{18}$ alcohols, styrenes, vinyl acetate, alkyl methacrylates, among others. Compositions containing such grafted silicone polymers provide excellent hair care and styling products which impart good sensory feel and softness to the hair.

International Patent Application Publication WO2004/065430 discusses the preparation of surface active compounds comprising polyolefin succinic anhydride compounds of low color and their use in various applications including personal care products, coatings, and light colored lubricants and fuels. The polyolefin succinic anhydride compounds are the product of reacting a polyolefin, preferably with at least 75 mole % derived from isobutylene and at least 45 mole % having a terminal vinylidene group, with maleic anhydride or fumaric acid, or esterification products of either with $C_{1-8}$ or $C_{10}$ alcohols. These polyolefin succinic anhydride compounds were found to impart a very desirable feel to human skin when applied in an oil or water-based personal care formulations such as skin lotions and soaps, hair shampoos and conditioners, shave creams and gels, facial products and cosmetics.

International Patent Application Publication WO2011034836A1 describes a class of silane containing polyolefins, for example, polyethylenes grafted with vinyl (polyalkoxy)silane monomers (i.e., vinyltrimethoxysilane) which are suitable for forming melt-shaped articles such as components for wires and cables. Upon curing, these compounds produce a stable thermoplastic compositions having improved compatibility between the silicone and polyolefin phases therein.

The present invention addresses the problem of providing formulations having improved sensory feel, while retaining other desired characteristics including spreadability and non-tacky feel on skin, by including silicone modified polyolefins which comprise a functionalized polyolefin and a functionalized silicone polymer. The silicone modified polyolefins can be swelled or dissolved in a carrier fluid to produce formulations having a soft, silky, and smooth feel and are easily spreadable and non-tacky on skin. It is believed that the silicone modified polyolefins may be used in many surface treatments where soft touch sensory characteristics are favored, including personal care, coatings, fabric care, and leather treatments.

SUMMARY OF THE INVENTION

The present invention provides a personal care formulation comprising a silicone modified polyolefin and a carrier. The silicon modified polyolefin is the reaction product of: (i) at least one functionalized polyolefin comprising polymerized units derived from one or more olefin monomers and having one or more functional groups; and (ii) at least one functionalized silicone polymer comprising polymerized units derived from one or more siloxanes having one or more functional groups.

The present invention also provides a method for treating the body which comprises applying the aforesaid personal care formulation externally to the body.

The present invention further provides a method for improving the sensory feel of personal care formulations comprising including one or more silicone modified polyolefins in said personal care formulations, wherein each of said one or more silicone modified polyolefins is the reaction product of: (i) at least one functionalized polyolefin comprising polymerized units derived from one or more olefin monomers and having one or more functional groups; and (ii) at least one functionalized silicone polymer comprising polymerized units derived from one or more siloxanes and having one or more functional groups.

In some embodiments, the one or more functional groups are selected from the group consisting of: hydroxyl (—OH), carboxylic acid (—C(=O)OH), ester (—C(=O)OR), anhydride (cyclic —CO(O)CO—), amino (—NH), silane (—SiH), vinyl (—C=C), epoxide (cyclic —COC—), halogens (—Cl, —Br, —I), silicon hydride (≡SiH), thiol (—SH), alkyne (—C≡C—) and azide (—N=N=N—).

In some embodiments the one or more olefin monomers of the functionalized polyolefins are selected from $C_2$-$C_{40}$ olefins.

In some embodiments, the functionalized polyolefin has silane functional groups which are derived from vinyltrialkoxysilanes.

In some embodiments, the one or more siloxanes of the functionalized silicone polymers are dialkylsiloxanes and the one or more functional groups are derived from monomers selected from the group consisting of polymerizable amines and polymerizable silanols.

BRIEF DESCRIPTION OF THE DRAWINGS

A more complete understanding of the present invention will be gained from the embodiments discussed hereinafter and with reference to the accompanying FIGURE which is a plot showing that skin care lotions of the present invention exhibit lower friction than the prior art at multiple normal loads, meaning that the skin care lotions of the present invention are less tacky and easier to spread.

DETAILED DESCRIPTION OF THE INVENTION

The following terms, phrases and meanings are used hereinafter.

As used herein, "ambient conditions" and like terms means temperature, pressure and humidity of the surrounding area or environment of an article. The ambient conditions of a typical office building or laboratory include a temperature of 23° C. and atmospheric pressure.

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the component amounts of the composition and various process parameters.

"Polymer" means a compound prepared by reacting (i.e., polymerizing) monomers, as well as oligomers and other polymers, whether of the same or a different types. The generic term polymer thus embraces the term "homopolymer," usually employed to refer to polymers prepared from only one type of monomer, and the terms "copolymer" and "interpolymer" which are polymers prepared by the polymerization of two or more different types of monomers, oligomers and/or polymers. As will be readily recognized by persons of ordinary skill in the relevant art, oligomers are simply small polymers, i.e., having a smaller number (i.e., 2-100,000) of repeated monomer units.

"Olefins," also referred to herein as alkenes or alkene monomers, are unsaturated chemical compounds containing at least one carbon-to-carbon double bond, the simplest of which conform to the general formula $C_nH_{2n}$, where n is a positive non-zero integer.

The phrase "comprising polymerized units derived from" as used hereinafter describes a polymer in terms of its constituent monomers. For example, a polymer comprising polymerized units derived from a polyolefin means that the polymer was formed from the polymerization reaction of at least one olefin monomer.

"Polyolefins" are polymers containing units derived from at least one type of olefin, typically a $C_2$-$C_{40}$ olefin, such as ethylene, propylene, butylene, pentene, hexane, etc. For example, polyethylene is a polymer which contains units derived from ethylene monomers, and typically comprises at least 50 mole percent (50 mol %) units derived from ethylene. Similarly, polypropylene contains units derived from propylene monomers, typically at least 50 mol % propylene.

"Blend," "polymer blend" and like terms mean a blend of two or more polymers. Such a blend may or may not be miscible. Such a blend may or may not be phase separated. Such a blend may or may not contain one or more domain configurations, as determined from transmission electron spectroscopy, light scattering, x-ray scattering, and any other method known in the art.

"Catalytic amount" means an amount of catalyst necessary to promote the crosslinking of an ethylene-vinylsilane polymer at a detectable level, preferably at a commercially acceptable level.

"Functional compounds" means compounds having one or more functional groups thereon and include functional monomers, as well as non-polymerizable compounds, which are or comprise functional groups. "Functional monomers" are generally ethylenically unsaturated monomers having at least one functional group. In either case, the functional groups include, for example, without limitation, hydroxyl (—OH), carboxylic acid (—C(=O)OH), ester (—C(=O)OR), anhydride (cyclic —CO(O)CO—), amino (—NH), silane (—SiH), vinyl (—C=C), epoxide (cyclic —COC—), halogens, (—Cl, —Br, —I), thiol (—SH), silicon hydride (≡SiH), alkyne (—C≡C—) and azide (—N=N=N—). The silicone hydride (≡SiH) functional group is similar to the silane (—SiH) functional group, but it is found on the backbone of silicone polymers, where instead of an R group, a hydrogen atom is bonded directly to a silicon atom of the backbone chain (see R groups defined for Formula B hereinbelow where silicone polymers are discussed).

"Crosslinked" mean that the polymer has been subjected or exposed to a treatment (e.g., heat, presence of free radicals, light, exposure to water, etc.) which induced reaction and bonding between functional groups of the polymer and other functional groups either within the same polymer, or of other functionalized polymers. The bonding need not be covalent bonding, but may also be ionic bonding or other electrochemical affinity between molecules or portions thereof, such as reactive functional groups. Furthermore, a polymer need not have all, or even most, of its functional groups reacted with other functional groups, to be considered a "crosslinked" polymer. A polymer may be considered "crosslinked" even when a small, or very small, portion of its functional groups are reacted with other functional groups.

"Crosslinkable" means that the polymer has not yet been crosslinked or bonded, but does comprise functional groups which will cause or promote crosslinking upon subjection or exposure to such treatment (e.g., exposure to water, heating, etc.).

As used herein, a "reaction product" is a compound resulting from the reaction of one molecule with another, where one or more of the molecules may be polymers, oligomers, macromolecules or smaller molecules and where the reaction may but does not have to result in covalent bonding. The reaction may also result in ionic bonding or other electrochemical bonds between molecules or portions thereof, such as reactive functional groups.

The term "personal care formulation" as used hereinafter means a mixture or blend of compounds or ingredients which is suitable for external application to the body to deliver therapeutic or cosmetic compounds to skin and hair and may be in the form of creams, gels, lotions, liquids, sprays, powders, mousses and foams. Personal care formulations may be of the leave-on or rinse-off types, depending on their purpose and the types of compounds to be delivered. Specific products made from personal care formulations include, without limitation: deodorants, antiperspirants, shaving creams or gels, skin lotions, bath and shower soaps and lotions, cleansing products, hair care products such as shampoos, conditioners, styling mousses, styling sprays, and hair color products; manicure products such as nail polish, nail polish remover, nail creams and lotions; protective creams and sprays such as sunscreen, insect repellent and anti-aging products, color cosmetics such as lipsticks, foundations, eye liners, eye shadows, blushes, as well as delivery vehicles for fragrances, or for drug delivery systems for topical application of medicinal compositions to the skin.

The present invention provides a personal care formulation comprising a carrier and a silicone modified polyolefin which is the reaction product of a functionalized polyolefin and a functionalized silicone polymer. The functionalized polyolefin comprises polymerized units derived from one or more olefin monomers and has one or more functional groups. The functionalized silicone polymer comprises polymerized units derived from one or more siloxanes and also has one or more functional groups. The one or more functional groups, regardless of whether they are on the polyolefin or the silicone polymer, include, for example, without limitation, hydroxyl (—OH), carboxylic acid (—C(=O)OH), ester (—C(=O)OR), anhydride (cyclic —CO(O)CO—), amino (—NH), silane (—SiH), vinyl (—C=C), epoxide (cyclic —COC—), halogens, (—Cl, —Br, —I), thiol (—SH), silicon hydride (≡SiH), alkyne (—C≡C—) and azide (—N=N=N—).

Personal care formulations which include silicone modified polyolefins in accordance with the present invention have improved sensory feel, i.e., softness and smoothness, as well as the desired degrees of other characteristics, including spreadability, non-tackiness and absorption.

There are many possible options for the compositions of the functionalized polyolefin and the functionalized silicone polymer, including what types of functional groups are on each polymer used to prepare the silicone modified polyolefins useful in the various embodiments of the present invention. One requirement, however, is that the functional groups of the functionalized polyolefin and the functional groups on the functionalized silicone polymer are reactive with one another. Thus, as will be readily apparent to persons of ordinary skill in the relevant art, selection of which functional groups are on the functionalized polyolefin and which are on the functionalized silicone polymer depends on considerations relating to which functional groups will react with one another to form the silicon modified polyolefins, as well as the particular compositions of polyolefin and silicone polymer being used and the particular type of formulation into which the resulting silicone modified polyolefin is to be blended.

The personal care formulation according to the present invention may further comprise a fluid carrier, such as aromatic or aliphatic hydrocarbons, alcohols, aldehydes, ketones, amines, esters, oleochemically derived oils, i.e., sunflower oil, ethers, glycols, glycol ethers, or silicone oils. The personal care formulation may also comprise the silicone modified polyolefin simply dispersed in an aqueous carrier, such as water. The resulting products deliver a soft, silky, and smooth feel on skin that are easily spreadable and non-tacky on the skin.

A method for improving the sensory feel of personal care formulations is also provided by the present invention and comprises including one or more silicone modified polyolefins in said formulations.

The present invention also provides a method for treating bodily surfaces, such as skin, hair and nails, which comprises applying one or more of the above-described personal care formulations externally to the bodily surfaces.

The functionalized polyolefins may be synthesized by copolymerizing one or more olefins with one or more functional monomers, or by grafting the one or more functional monomers to a polyolefin polymer. Furthermore, if the polyolefin already has functional groups, functional compounds which are not polymerizable may be reacted or added to the already-present functional groups on the polyolefin to make functionalized polyolefins suitable for synthesizing the silicone modified polyolefins useful in the present invention. Thus, the functional groups of the functionalized polyolefin may be integral with the backbone of the polyolefin, or they may be bonded to the backbone of the polymer, either directly as terminal groups or side groups, or indirectly to side groups or chains of the polyolefin.

The functionalized silicone polymers, on the other hand, may be produced by grafting one or more functional monomers to a silicone polymer, or where the silicone polymer already has functional groups, functional compounds which are not polymerizable may be reacted or added to the already-present functional groups on the silicone polymer to make functionalized silicone polymers suitable for synthesizing the silicone modified polyolefins useful in the present invention. Thus, the functional groups of the functionalized silicone polymer may be bonded either as terminal groups directly to the silicone polymer backbone, or indirectly to the organic side groups or chains of the silicone polymer.

Functionalized polyolefins and functionalized silicone polymers useful for synthesizing silicone modified polyolefins suitable for use in the personal care formulations according to the present invention will now be described in further detail.

Functionalized Polyolefin

Functionalized polyolefins useful for preparing the silicone modified polyolefin suitable for use in the present invention comprise polymerized units derived from one or more olefin monomers and have one or more functional groups. In some embodiments, the polyolefins further comprise polymerized units of monomers other than olefin monomers. Polyolefins useful in the practice of this invention include homopolymers and copolymers, and they may be random or blocked, as well as linear or branched.

The one or more olefin monomers may be selected from $C_2$-$C_{40}$ olefins, such as $C_2$-$C_{35}$ olefins, such as $C_2$-$C_{20}$ olefins such as $C_2$-$C_{10}$ olefins or more preferably $C_2$-$C_8$ olefins. The olefin monomers may be α-olefins and, preferably, are $C_{2-40}$ linear, branched or cyclic α-olefins. Non-limiting examples of $C_{2-40}$ linear and branched α-olefins include ethylene, propene, 1-butene, 4-methyl-1-pentene, 1-hexene, 1-octene, 1-decene, 1-dodecene, 1-tetradecene, 1-hexadecene, and 1-octadecene. The α-olefins may also contain a cyclic structure such as cyclohexane or cyclopentane, resulting in an α-olefin such as 3-cyclohexyl-1-propene (allyl cyclohexane) and vinyl cyclohexane. Although not α-olefins in the classical sense of the term, for purposes of this invention certain cyclic olefins, such as norbornene and related olefins, particularly 5-ethylidene-2-norbornene, are α-olefins suitable for inclusion in the polyolefins, which otherwise comprise at least 50 weight percent acyclic $C_2$-$C_{40}$ α-olefins. Similarly, styrene and its related olefins (for example, α-methylstyrene, etc.) are α-olefins for purposes of this invention.

As already discussed above, the functional compounds suitable for synthesizing the functionalized polyolefin may be functional monomers which are themselves polymerizable, or compounds having functional groups but which are not polymerizable, depending on whether the functional compounds are to be copolymerized with olefin monomers or grafted to, or otherwise reacted with, existing polyolefin polymers, to produce the functionalized polyolefin. Suitable functional groups include, for example, without limitation, hydroxyl (—OH), carboxylic acid (—C(=O)OH), ester (—C(=O)OR), anhydride (cyclic —CO(O)CO—), amino (—NH), silane (—SiH), vinyl (—C=C), epoxide (cyclic —COC—), halogens, (—Cl, —Br, —I), silicon hydride (≡SiH), thiol (—SH), alkyne (—C≡C—) and azide (—N=N=N—).

For example, without limitation, when allyl alcohol (2-propenol), or a hydroxyl alkyl acrylate ester, such as hydroxyl ethyl acrylate, or an unsubstituted or substituted silanol, is used as the functional compound, the resulting functionalized polyolefins will include hydroxyl functional groups.

Similarly, when an unsaturated carboxylic acid such as, without limitation, acrylic acid and methacrylic acid, is used as the functional compound, the resulting functionalized polyolefins will have carboxyl functional groups.

Where an unsaturated carboxylic anhydride such as, without limitation, maleic anhydride, citraconic anhydride, itaconic anhydride, glutaconic anhydride and 2,-3-dimethylmaleic anhydride, is used as the functional compound, the resulting functionalized polyolefins will have anhydride functional groups.

Furthermore, where silane is used as the functional compound, the resulting functionalized polyolefins will have silane functional groups. For example, where it is desired to copolymerize a silane with one or more olefin monomers, or graft to, or crosslink it with, a pre-existing polyolefin, such vinyl silanes will have the following Formula A:

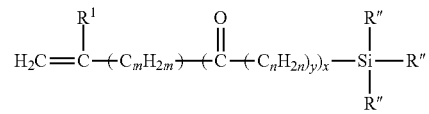

in which $R^1$ is a hydrogen atom or methyl group; x and y are 0 or 1, with the proviso that when x is 1, y is 1; m and n are independently an integer from 1 to 12 inclusive, preferably 1 to 4; and each R" is, independently, a hydrolyzable organic group selected from the group consisting of: an alkoxy group having from 1 to 12, preferably from 1 to 4, carbon atoms, an aryloxy group, an araloxy group, an aliphatic acyloxy group having from 1 to 12 carbon atoms, an amino group, a substituted amino group, and a lower alkyl group having 1 to 6 carbon atoms inclusive, with the proviso that not more than one of the R" groups is an alkyl.

More particularly, alkoxy groups having from 1 to 12 carbon atoms that are suitable for the R" groups of the silane include, for example without limitation, methoxy, ethoxy, butoxy and pentoxy groups. As further non-limiting examples, a suitable aryloxy group may be a phenoxyl group, and a suitable araloxy group may be a benzyloxy group. Aliphatic acyloxy groups having from 1 to 12 carbon atoms that are suitable for the R" groups of the silane include, for example without limitation, formyloxy, acetyloxy and propanoyloxy groups. Suitable substituted amino groups for the R" groups of the silane include, for example without limitation, alkylamino and arylamino groups. Only one of the three R" groups may be a lower alkyl group having 1 to 6 carbon atoms, i.e., one methyl, ethyl, propyl, butyl, pentyl or hexyl group.

Suitable silanes include, for example, without limitation, unsaturated silanes that comprise an ethylenically unsaturated hydrocarbyl group, such as a vinyl, allyl, isopropenyl, butenyl, cyclohexenyl or gamma-(meth)acryloxy allyl group, and a hydrolyzable group, such as, for example, a hydrocarbyloxy, hydrocarbonyloxy, or hydrocarbylamino group. Examples of hydrolyzable groups include methoxy, ethoxy, formyloxy, acetoxy, proprionyloxy, and alkyl or arylamino groups. Preferred silanes are the unsaturated alkoxy silanes which can be grafted onto the polymer or copolymerized in-reactor with other monomers (such as ethylene and acrylates). These silanes and their method of preparation are more fully described in U.S. Pat. No. 5,266,627 to Meverden, et al. Vinyl trimethoxy silane (VTMS), vinyl triethoxy silane (VTES), vinyl triacetoxy silane, gamma-(meth)acryloxy propyl trimethoxy silane and mixtures of these silanes are the preferred vinyl silanes for use in this invention.

The amount of vinyl silane used in the practice of the present invention can vary widely depending upon the nature of the polymer, the silane, the processing or reactor conditions, the grafting or copolymerization efficiency, the ultimate application, and similar factors, but typically at least 0.1, preferably at least 0.5, weight percent is used. Considerations of convenience and economy are two of the principal limitations on the maximum amount of silane crosslinker used in the practice of this invention, and typically the maximum amount of silane crosslinker does not exceed 50, preferably it does not exceed 15, weight percent, based on the total amount of silane-containing polyolefin.

Furthermore, when an amine such as, without limitation, allyl amine, aminobutene, or aminohexane, is used as the functional compound, the resulting functionalized polyolefins will have amino functional groups.

Where a polyethylenically unsaturated monomer, i.e., dienes, trienes, etc., such as, for example, allyl methacrylate, diallyl phthalate, vinyl crotonate, or divinyl benzene, is used as the functional compound, the resulting functionalized polyolefins will have vinyl functional groups.

Similarly, where an epoxide such as, without limitation, glycidyl acrylate or glycidyl methacrylate, is used as the functional compound, the resulting functionalized polyolefins will have epoxide functional groups.

Where a thiol compound such as, without limitation, a mercaptan or an allyl mercaptan, is used as the functional compound, the resulting functionalized polyolefins will have thiol functional groups.

The copolymerization, grafting, or other reaction between the functional compounds and olefins monomers or existing polyolefins to produce suitable functionalized polyolefins may be accomplished by any method known now or in the future to persons of ordinary skill in the relevant art.

Without limiting the present invention, when the functional compounds are either copolymerized or grafted, to make the functionalized polyolefins, the reaction schemes provided below provide the general reaction process steps. While there are many possible choices for the particular reactants, the following reaction schemes show olefins, other polymerizable monomers different from the olefins, and either a silane or anhydride as the functional compound to synthesize either silane functionalized polyolefin or anhydride functionalized polyolefin, respectively.

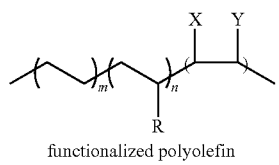

functionalized polyolefin

As shown above in Reaction Scheme I, when copolymerization technology is used, some number (m) of ethylene monomers, some number (n) of other α-olefins different from the ethylene monomers (for example, where R is methyl, hexyl, octyl, etc.), and an ethylenically unsaturated functional monomer are present together in a reaction mixture and are polymerized together, in a single reactor, to form the functionalized polyolefin polymer having the functional groups of the functional monomer.

For example, in Reaction Scheme I, where the functional monomer is a vinyl silane, X would be SiR"3 and Y would be hydrogen or an alkyl and the functionalized polyolefin would be of the following Structure A:

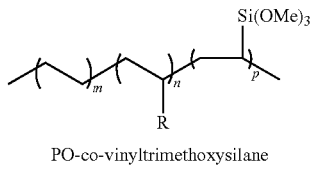

PO-co-vinyltrimethoxysilane

Alternatively, in Reaction Scheme I, where the functional monomer is maleic anhydride, X would be C(O) and Y would be —C(O)—O— and the functionalized polyolefin would be of the following Structure B:

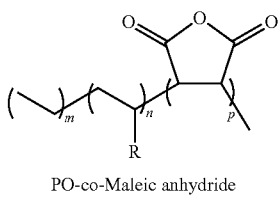

PO-co-Maleic anhydride

Reaction Scheme I

Copolymerization

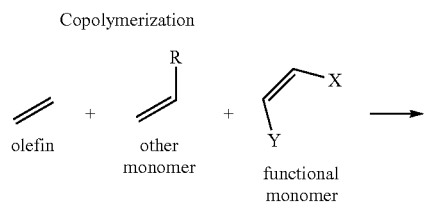

Reaction Scheme II

Grafting (polymerization)

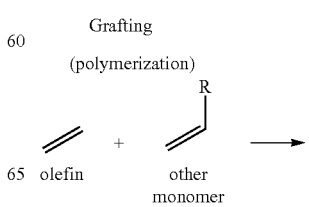

-continued
(grafting)

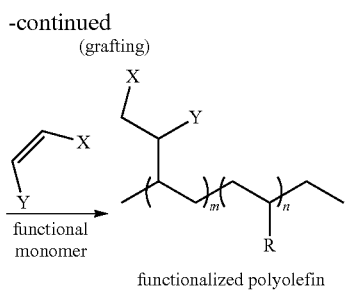

As shown above in Reaction Scheme II, when the functionalized polyolefin is synthesized using grafting technology, in a first step, some number (m) of olefin monomers and some number (n) of other monomers different from the olefin monomers (for example, R may be methyl, hexyl or octyl) are first polymerized together to form a polyolefin polymer. In a second step, the polyolefin is then grafted with an ethylenically unsaturated functional monomer, to form the functionalized polyolefin having the functional groups of the functional monomer. For example, in Reaction Scheme II, where the functional monomer is a vinyl silane, X would be SiR"3 and Y would be hydrogen or an alkyl and the functionalized polyolefin would be of the following Structure C:

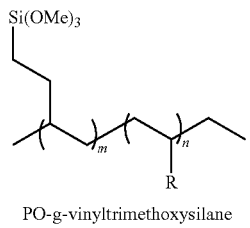

PO-g-vinyltrimethoxysilane

Alternatively, in Reaction Scheme II, where the functional monomer is maleic anhydride, X would be C(O) and Y would be —C(O)—O— and the functionalized polyolefin would be of the following Structure D:

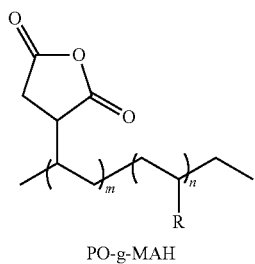

PO-g-MAH

Furthermore, the compound represented by Structure D above, where the olefin monomer is ethylene and the other monomer is octene, is commercially available from The Dow Chemical Company of Midland, Mich., USA under the tradename AMPLIFY GR, and is suitable, as is, for use as the functionalized polyolefin.

In general, the functionalized polyolefins suitable for use in the present invention may be produced using conventional polyolefin polymerization technology, e.g., high-pressure, Ziegler-Natta, metallocene, constrained geometry catalysis, solution, reactive extrusion, among others well known to persons of ordinary skill in the relevant art. In one embodiment, particularly where the functionalized polyolefin is prepared by copolymerization of olefin monomers and ethylenically unsaturated functional monomers, high pressure reactor polymerization technology may be employed. In another embodiment, the polyolefin may be prepared using a mono- or bis-cyclopentadienyl, indenyl, or fluorenyl transition metal (preferably Group 4) catalysts or constrained geometry catalysts (CGC) in combination with an activator, in a solution, slurry, or gas phase polymerization process.

In still another embodiment, such as where one or more ethylenically unsaturated functional monomers are to be grafted onto an existing polyolefin, functionalized polyolefins suitable for the present invention are prepared by a melt phase reactive extrusion process, for example, using twin screw extruder apparatus under high pressure and temperature conditions.

In general, polymerization can be accomplished at conditions well-known in the art for Ziegler-Natta or Kaminsky-Sinn type polymerization reactions, that is, at temperatures from 0 to 250° C., preferably from 30 to 200° C., and pressures from atmospheric to 10,000 atmospheres (1013 megaPascal (MPa)). Suspension, solution, slurry, gas phase, solid state powder polymerization or other process conditions may be employed, if desired. The catalyst can be supported or unsupported, and the composition of the support can vary widely. Silica, alumina or a polymer (especially poly(tetrafluoroethylene) or a polyolefin) are representative supports, and desirably a support is employed when the catalyst is used in a gas phase polymerization process. The support is preferably employed in an amount sufficient to provide a weight ratio of catalyst (based on metal) to support within a range of from 1:100,000 to 1:10, more preferably from 1:50,000 to 1:20, and most preferably from 1:10,000 to 1:30. In most polymerization reactions, the molar ratio of catalyst to polymerizable compounds employed is from $10^{-12}:1$ to $10^{-1}:1$, more preferably from $10^{-9}:1$ to $10^{-5}:1$.

Inert liquids may serve as suitable solvents for polymerization. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes; and aromatic and alkyl-substituted aromatic compounds such as benzene, toluene, xylene, and ethylbenzene. Selection of a suitable solvent for polymerization is well within the ability of persons of ordinary skill in the relevant art.

While various kinds of polyolefins are suitable for use in the present invention, as stated above, polyethylenes are particularly suitable for synthesizing the silicone modified polyolefins used in the surface treatment composition of the present invention. As will be recognized by persons of ordinary skill in the relevant art, use of other types of polyolefins are equally acceptable for the present invention, and much of the following detailed discussion will be instructional and analogously applicable to other types of polyolefins when used in connection with the present invention.

The polyethylene may comprise polymerized units derived only from ethylene monomers (—$CH_2$—$CH_2$—), or it may comprise polymerized units derived from ethylene and one or more other olefin monomers. Suitable ethylene/α-olefin copolymers include those having an ethylene content of at least 50 wt % and an α-olefin content of at least about 15, preferably at least about 20 and even more preferably at least about 25, wt % based on the total weight of the copolymer. These copolymers typically have a non-ethylene α-olefin content of less than about 50, preferably less than about 45, more preferably less than about 40 and even more preferably less than about 35, wt % based on the total weight of the copolymer. The α-olefin content is measured by $^{13}C$ nuclear magnetic resonance (NMR) spectroscopy using the procedure described in Randall (Rev. Macromol. Chem. Phys., C29 (2&3)).

Illustrative ethylene copolymers include ethylene/propylene, ethylene/butene, ethylene/1-hexene, ethylene/1-octene, ethylene/styrene, and the like. Illustrative terpolymers include ethylene/propylene/1-octene, ethylene/propylene/butene, ethylene/butene/1-octene, ethylene/propylene/diene monomer (EPDM) and ethylene/butene/styrene.

For example, ethylene-octene copolymers are commercially available under the tradename ENGAGE from Dow Chemical of Midland, Mich., U.S.A. and may be grafted with maleic anhydride to serve as the functionalized polyolefins useful for synthesizing silicone modified polyolefins suitable for use in the present invention. Also, polyethylene polymers already functionalized with maleic anhydride (see Structure D above) are available under the tradename AMPLIFY from The Dow Chemical Company and would be suitable for use in preparing the silicone modified polyolefins.

The ethylene polymers used in the practice of this invention can be used alone or in combination with one or more other ethylene polymers, e.g., a blend of two or more ethylene polymers that differ from one another by monomer composition and content, catalytic method of preparation, etc. Furthermore, ethylene polymers and ethylene/α-olefin co polymers may be used in combination with one or more other polyolefin polymers, such as those defined hereinabove.

Examples of ethylene polymers made with high pressure processes include (but are not limited to) low density polyethylene (LDPE), ethylene silane reactor copolymer (such as SILINK available from The Dow Chemical Company), ethylene vinyl acetate copolymer (EVA), ethylene ethyl acrylate copolymer (EEA), and ethylene silane acrylate terpolymers.

Functionalized Silicone Polymer

Functionalized silicone polymers useful for preparing silicone modified polyolefins suitable for use in the present invention comprise polymerized units derived from one or more siloxanes having organic side chains and have one or more functional groups. Such compounds may also be referred to as functionalized "polysiloxanes." Although persons of ordinary skill may, more technically, describe the functionalized silicone polymers discussed herein as oligomers, rather than polymers, since the term "polymer" has been defined herein as including oligomers, the terms "silicone polymers" or "polysiloxanes" will be used hereinafter.

Siloxanes having organic side chains and which are suitable for synthesizing the functionalized silicone polymers useful in the present invention have the following general Formula B:

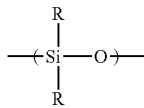

wherein each R is, independently, hydrogen, an organic group selected from the group consisting of: $C_1$-$C_{12}$ alkyls, $C_2$-$C_{12}$ alkenyls, aryls, fluorine substituted $C_1$-$C_{12}$ alkyls, and derivatives thereof which comprise one or more functional groups selected from the group consisting of hydroxyl groups, amino groups, vinyl groups, and combinations thereof. For example without limitation, each R may be hydrogen, methyl, ethyl, n-propyl, isopropyl, n-butyl, sec-butyl, dodecyl, vinyl, allyl, phenyl, naphthyl, tolyl, and 3,3,3-trifluoropropyl. In some preferred embodiments, the silicone polymers are polydialkylsiloxanes which comprise polymerized units derived from dialkylsiloxanes having from 2 to 100,000 or more units of the formula —$R_2SiO$— in which each R is a $C_1$-$C_{12}$ alkyl. In some especially preferred embodiments, each R is selected from the group consisting of: methyl, ethyl and isopropyl. Preferred silicone polymers include polydimethylsiloxane (PDMS) and polydiethylsiloxane (PDES).

Functional compounds suitable for preparing the functionalized silicone polymers are the same as discussed hereinabove, i.e., one or more functional monomers or other non-polymerizable compounds having one or more functional group. Suitable functional groups include, for example, without limitation, hydroxyl (—OH), carboxylic acid (—C(=O)OH), ester (—C(=O)OR), anhydride (cyclic —CO(O)CO—), amino (—NH), silane (—$SiH_3$), alkylsiloxane ($Si(OR)_3$), vinyl (—C=C), epoxide (cyclic —COC—), halogens, (—Cl, —Br, —I), silicon hydride (≡SiH), thiol (—SH), alkyne (—C≡C—) and azide (—N=N=N—).

The functional compounds may be reacted with, e.g., grafted onto, existing silicone polymers to produce suitable functionalized silicone polymers. Such functionalized silicone polymers may have their functional groups bonded as terminal groups to one or both ends of the polymer backbone, or to the organic side chains, as shown below:

Structure E

Chain Functionalized Silicone Polymer

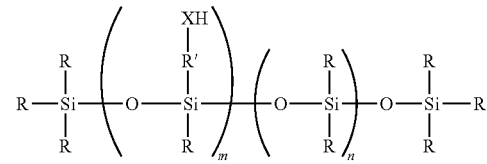

For example, in Structure E, R may be methyl, R' may be an alkyl. Furthermore, where a polymerizable amine or allyl alcohol was used as the ethylenically unsaturated functional monomer, X would be —NH or —O, respectively.

Structure F

End Functionalized Silicone Polymer

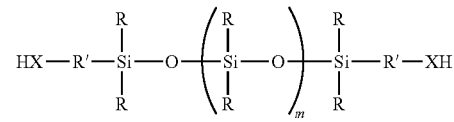

Similarly, in Structure F, R may be methyl, ethyl, n-propyl, etc., each R' is optional and may be a $C_1$-$C_{10}$ alkyl, and X is optional and may be the same or different and selected from —NH or —O, such as when a polymerizable amine or allyl alcohol, respectively, was used as the ethylenically unsaturated functional monomer In some embodiments, the functionalized silicone polymer is a functionalized poly(dialkylsiloxane) synthesized by grafting one or more ethylenically unsaturated functional monomers onto a poly(dialkysiloxane). For example, the functionalized silicone polymer may be silanol terminated polydimethylsiloxane (t-hydroxyl-PDMS), or mono- or bis-aminopropyl terminated polydimethylsiloxane (t-amine-PDMS), or vinyl terminated polydimethylsiloxane (t-vinyl-PDMS). Additionally, suitable functionalized silicone polymers include, without limitation, silanol grafted polydimethylsiloxane (silanol-g-PDMS), or mono- or bis-aminopropyl terminated polydimethylsiloxane (amine-g-PDMS), or vinyl terminated polydimethylsiloxane (vinyl-g-PDMS). Non-limiting examples of commercially available functionalized polydialkylsiloxanes suitable for use in the present invention include silanol-terminated polydimethylsiloxane DMS-15 (molecular weight on number basis, MWn, of 2,000-3,500, viscosity of 45-85 centistokes, —OH level of 0.9-1.2%) available from Gelest Corp., and Silanol Fluid 1-3563 (viscosity 55-90 centistokes, —OH level of 1-1.7%) available from Dow Corning Corp. of Midland, Mich., USA.

In general, functionalized silicone polymers useful for preparing the silicone modified polyolefins used in the present invention may be produced using any technique known now or in the future to persons of ordinary skill in the relevant art. For example, a selected silane-containing silicone polymer, such as a silane-containing polydialkylsiloxane, may be functionalized with one or more amine end groups by reacting it with an excess of an amine-containing compound, such as an allylamine, in a reaction vessel, in the presence of a platinum-based or other effective catalyst, with heat (between 80 and 140° C.) and continuous stirring, to produce an amine functionalized polydialkylsiloxane.

Inert liquids may serve as suitable solvents for the aforesaid functionalization reaction, but are not necessary. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes; and aromatic and alkyl-substituted aromatic compounds such as benzene, toluene, xylene, and ethylbenzene. Selection of a suitable solvent, or no solvent, for functionalization is well within the ability of persons of ordinary skill in the relevant art.

Synthesis of Silicone Modified Polyolefins

At least one functionalized polyolefin and at least one functionalized silicone polymer are reacted with one another, either with or without a catalyst, and with or without a solvent, to form the silicone modified polyolefins suitable for use in the personal care formulations according to the present invention. Once the types of functionalized polyolefin and functionalized silicone polymer have been selected, they may be reacted by any means known now or in the future to persons of ordinary skill in the relevant art. For example, without limitation, the functionalized polyolefin may be first dissolved in a suitable solvent, such as toluene, dodecane, etc., in a vessel and then heated (temperature between 50 and 250° C.) and stirred. The functionalized silicone polymer is then added to the heated polyolefin, while stirring continues. Alternatively, the synthesis may be performed without any solvent. The synthesis may also be performed by allowing the heated polyolefin to cool before adding the silicone polymer.

The amount of functionalized silicone polymer reacted with the functionalized polyolefin can vary widely depending upon the nature of the functionalized polyolefin and the types of functional groups it contains, the processing or reactor conditions, the ultimate application, and similar factors. Nonetheless, typically at least 0.1 wt %, or at least 1 wt %, or at least 5 wt %, or even 10 wt %, of total functionalized silicone polymer is used, based on the total weight of the silicone modified polyolefin. Considerations of convenience and economy are two of the principal limitations on the maximum amount of silicone polymer used in the practice of this invention, and typically the maximum total amount of functionalized silicone polymer is no more than 99 wt %, such as no more than 75 wt %, or no more than 50 wt %, or even no more than 30 wt %, based on the total weight of the silicone modified polyolefin.

As already mentioned earlier, the selection of which functional compounds to use for preparing each of the functionalized polyolefin and functionalized silicone polymer will depend upon the type of polyolefin and silicone polymer desired to be in the final silicone modified polyolefin product, which in turn will depend on the intended application of the formulation to which it will be added. Furthermore, consideration of which functional groups will react and bond as desired with one another is appropriate when selecting which functional compounds to use to prepare each of the functionalized polyolefin and functionalized silicone polymer.

For example, where the functionalized polyolefin is an ethylene-octene polymer with maleic anhydride functionality, the functionalized silicone polymer should be prepared from a functionalized silicone polymer that is grafted with a functional group that will be capable of reacting with anhydride functional groups, such as, for example, an alcohol or an amine group.

In some preferred embodiments, the silicone modified polymer is the reaction product of a polyethylene having silane functional groups, such as vinyltriethoxysilane (PE-g-VTES), and a hydroxyl functionalized polydialkylsiloxane, such as silanol-terminated polydimethylsiloxane (t-silanol-PDMS).

In other preferred embodiments, the silicone modified polymer is the reaction product of a polyethylene having maleic anhydride functionality (also known as succinic anhydride functionalized polyolefins), such as an isobutylene-based polymer having anhydride functional groups (PiB-anhydride), and an amino functionalized polydialkylsiloxane, such as monoamino-terminated polydimethylsiloxane (t-amino-PDMS).

In still other preferred embodiments, the silicone modified polymer is the crosslinked reaction product of a polyethylene having maleic anhydride functionality (i.e., a succinic anhydride functionalized polyolefin), such as a poly(ethylene-co-octene) polymer grafted with maleic anhydride (PE-g-Mah), and an amino functionalized polydialkylsiloxane copolymer, such as (2-3% aminopropylmethylsiloxane)-(dimethylsiloxane) copolymer ((amino-PMS)-PDMS).

The resulting silicone modified polyolefins may be suspended into a carrier, such as hydrogenated polydecane, with heat, to form a paste before adding it to a formulation with suitable other ingredients for form a personal care formulation according to the present invention.

Preparation of Personal Care Formulations

The resulting silicone modified polyolefin may then be combined with an organic or aqueous carrier and optional other ingredients, to produce a personal care formulation having soft, silky, and smooth feel and which are easily spreadable and non-tacky. Suitable carriers include, for example without limitation, aromatic or aliphatic hydrocarbons, alcohols, aldehydes, ketones, amines, esters, oleochemically derived oils, i.e., sunflower oil, ethers, glycols, glycol ethers, or silicone oils, or water. The personal care formulation may be in the form of a powder, liquid, pellet, bead, oil gel, oil paste, or an aqueous dispersion. It may be combined with other ingredients, such as emollients (hydrocarbon oils, esters, natural oils, silicones), waxes, sensory modifiers, rheology modifiers, humectants (glycerin, etc), sunscreen actives, natural ingredients, bio-actives, colorants, hard particles, emulsifiers, solubilizers, and surfactants.

Persons of ordinary skill in the relevant arts will be able to determine what kinds of other ingredient should be combined with the polyolefin-silicone elastomer polymers in the personal care formulation, based upon what application is intended, i.e., skin, hair, nails, etc.

Where the personal care formulation is in the form of an oil gel/paste, the amount of polyolefin-silicone elastomer polymer included therein is typically 1 to 60, preferably 2 to 20% by weight, based on the total weight of the personal care formulation.

Where the personal care formulation is in the form of emulsion (lotion or cream), the amount of crosslinked silicone-modified polyolefin included therein is typically 0.1 to 60, preferably 1 to 40% by weight, based on the total weight of the personal care formulation.

Where the personal care formulation is in the form of aqueous product, the amount of polyolefin-silicone elastomer polymer included therein is typically 0.1 to 90, preferably 0.5 to 15% by weight, based on the total weight of the personal care formulation.

Since it is known that polyolefins and silicone polymers have low compatibility with one another, and have been observed to cause two phases to form when both are blended into personal care formulations, such as personal care products, it is surprising that the above-described silicone modified polyolefins form stable homogenous phase formulations and that the formulations actually have improved feel, along with all the other beneficial and preferred characteristics, as discussed in detail hereinabove.

EXAMPLES

Key Terminology

PTFE=polytetrafluoroethylene

PDMS=a silicone polymer, poly(dimethylsiloxane)

AMPLIFY=a polyolefin, maleic anhydride functionalized polyethylene polymers commercially available from The Dow Chemical Company of Midland, Mich., USA AFFINITY GA1950=linear ethylene/1-octene polymer available from The Dow Chemical Company ENGAGE 7447EL=copolymer of ethylene and octane available from DuPont Dow Elastomer LLC LILAC=a blend of $C_{14}$-$C_{22}$ alkanes commercially available from Sonneborn of Parsippany, N.J., USA Irganox B-225=phenolic antioxidant commercially available from BASF of Florham Park, N.J., USA MWn=molecular weight, number basis MWw=molecular weight, weight basis Example 1—Synthesis of a Functionalized Silicone Polymer MW=7000 Mono-Aminopropyl Terminated Poly(dimethylsiloxane)

The reactions were set up in a nitrogen purged glovebox. The catalyst $PtO_2$ (about 2 mg) was added to a 35 mL volume microwave reactor tube with an x-shaped PTFE-coated magnetic stirbar. Allylamine (1.6 mL) was combined with mono-silane terminated PDMS (13 g) in the tube. The tube was capped and placed in a CEM Discover microwave reactor. While stirring, the reaction was heated to 110° C. at 300 W over about 10 minutes. The reaction temperature was maintained at 110° C. while stirring. The internal pressure reached about 25 psig. After 1 hour, the reaction was cooled to room temperature and transferred to a nitrogen purged glovebox. The product mixture was filtered through a 20 micron polyethylene frit (a small amount of hexane was added to facilitate transfer of the polymer) and solvent was removed in vacuo. The resulting liquid was analyzed by 1H NMR spectroscopy (in C6D6 with a delay of 60 seconds). Nearly complete conversion (>98%) of the silane was seen, with the desirable amine product being formed. This reaction was run a total of 4 times to generate >50 g of product. The products were combined into a single batch.

Silicone Modified Polyolefins

Example 2—Synthesis of a Silicone Modified Polyolefin W/Solvent

AMPLIFY GR202-g-monoamino PDMS (PE-g-PDMS) (3.5 wt %) in Toluene

In a 2 L resin kettle equipped with a reflux condenser, an overhead stirrer and a thermocouple was placed AMPLIFY GR202 (192.0 g, 15.36 mmol anhydride). The polymer was dissolved in toluene (1400 mL) with rapid stirring at 100° C. Aminopropyl terminated poly(dimethylsiloxane) (7.51 mL of MWn=900 polymer, 7.68 mmol, 0.5 equiv) was added and stirring was maintained for 5 h. After that time, the reactor was cooled to 60° C. and acetone (700 mL) was added to precipitate the polymer. Cooling to ambient temperature was continued overnight. The polymer was collected on a Buchner funnel and allowed to air dry over the weekend. After purification by Soxhlet extraction, the polymer was dried in vacuo at 60° C.

Example 3—Synthesis of a Silicone Modified Polyolefin W/Solvent

AMPLIFY GR216-g-PDMS (2.8 wt %) in Toluene

In a 2 L resin kettle equipped with a reflux condenser an overhead stirrer and a thermocouple was placed AMPLIFY GR216 (152.0 g, 6.08 mmol anhydride). The polymer was dissolved in toluene (1200 mL) with rapid stirring at 100° C. Aminopropyl terminated poly(dimethylsiloxane) (5.95 mL of MWn=900 polymer, 6.08 mmol, 1 equiv) was added and stirring was maintained for 6 hours. After that time, the reactor was cooled to 45° C. and precipitation was attempted with acetone. Approximately 800 mL was added resulting only in the polymer becoming milky in appearance. The entire reaction mixture was poured into a PTFE dish and was allowed to evaporate over the weekend, then dissolved in hexanes at 60° C. to give a clear solution and re-precipitated with acetone/MeOH. The solid was collected by filtration and was air dried and then vacuum dried at 60° C. The material was then purified by Soxhlet extraction with acetone to give a fluffy elastic material. Analysis by 1H NMR (d1=30 s, 32 pulse) indicated 2.8 wt % PDMS incorporation

Example 4—Synthesis of a Silicone Modified Polyolefin W/Out Solvent

AMPLIFY GR202-g-PDMS Under Toluene-Free Conditions

AMPLIFY GR202 was dehydrated overnight at 150° C. under vacuum and 181 g of it was added to the 300 cc mixing bowl of a Haake polylab mixing system. The bowl temperature was at 180° C. while the paddles rotated at 70 rpm. Irganox B-225 (140 mg) was added to the fluxing polymer as a dry powder. The polymer was mixed for about 2 minutes. Monoaminopropyl-terminated PDMS (8 mL) was added dropwise to the mixing bowl. Torque was allowed to recover between additions of the PDMS. The addition took about 20 minutes. The resulting mixture was fluxed for an additional 7 minutes. The polymer was immediately removed from the Haake (yield=156 g). The polymer was cut into small pieces and pulverized in a Retsch mill.

Example 5—Synthesis of a Silicone Modified Polyolefin W/Solvent

In a 1 L kettle reactor was placed AFFINITY GA1950 (28.1 g) and ENGAGE-g-VTES (8.88 g). To the jar was added 322 mL of hexadecane to produce a 12.5 wt % solution. The reactor was fitted with an overhead stirrer, a nitrogen inlet (slow purge) and reflux condenser. A heating mantle was used to heat the stirred suspension to 180° C. After maintaining the homogeneous solution at 180° C. for 1 h, silanol-terminated PDMS (6.0 mL, 0.375 equiv relative to contained VTMS) was added via syringe. Stirring and heating was continued for a period of 90 minutes, after which the reactor contents were poured into a large jar and allowed to cool to ambient temperature producing a smooth gel.

Example 6—Synthesis of a Silicone Modified Polyolefin W/Controlled Crosslinking ENGAGE 8200-g-PDMS 480 mL of LILAC (Sonneborn CAS: 8042-47-5, a mixture of $C_{14}$-$C_{22}$ alkanes) was added to a large glass kettle mixer with an overhead stirrer. ENGAGE 8200 (23.5 g) and 700 melt index maleic anhydride grafted poly(ethylene-co-octene) (39 g) were added to the solvent at room temperature. While stirring, the mixture was heated to 170° C. in a heating mantle. A condenser attached to a nitrogen line was kept on top of the mixer. The mixture was stirred for a total of about 30 minutes. A total of 41 mL of (2-3% aminopropylmethylsiloxane)-(dimethylsiloxane) silicone copolymer (available from Gelest) was poured into the top of the reactor while stirring at about 170° C. The resulting mixture is stirred for about 10 minutes. The resulting solution is poured into a glass jar while hot and cooled to room temperature to form a transparent oil paste.

This method of preparing a silicone modified polyolefin was a controlled crosslinked method using a PDMS silicone that was functionalized with amine group along the backbone (benefit is lower cost). This method is enabled by the use of a low molecular weight maleic anhydride-grafted polyolefin (MW<20,000) as the primary polyolefin grafting agent, which enables formation of a polyolefin-graft-PDMS structure without deleterious levels of crosslinking. The method can be further used for additional crosslinking agents to control the level of crosslinking in the gel (such as high molecular weight MAH-grafted polyolefin to give chemical crosslinking or semi-crystalline polyolefins to give physical crosslinking).

Personal Care Formulations

TABLE I

Skin Lotion Formulations A and Comparative X

| Trade Name | INCI Name | Comparative Form. X wt % | Formulation A wt % |
|---|---|---|---|
| Phase I | | | |
| DI Water | Water | q.s. to 100 | q.s. to 100 |
| Glycerin | Glycerin | 2.00 | 2.00 |
| Keltrol CG-SFT (CP Kelco) | Xanthan Gum | 0.70 | 0.70 |
| Phase II | | | |
| Procol CS-20-D (Protameen) | Cetearyl Alcohol (and) Ceteareth 20 | 3.00 | 3.00 |
| RITA GMS (RITA) | Glyceryl Stearate | 2.00 | 2.00 |
| Super White Protopet (Sonneborn) | Petrolatum | 5.00 | 5.00 |
| Ritadecene 20 (RITA) | Hydrogenated Polydecene | 27.40 | |
| 18 wt % Polyolefin-g-PDMS oil paste based on Ex. 4 | | | 33.40 |
| Phase III | | | |
| Neolone PE (Dow) | Phenoxyethaol, Methylisothiazolinone | 0.60 | 0.60 |
| Citric Acid (50% Solution) | Citric Acid | pH = 5.5~6.5 | pH = 5.5~6.5 |

Formulation A—Containing 6% Solids of PE-g-PDMS (Ex4)

18 g of the PE-g-PDMS of Example 4 above was first dissolved in 82 g of hydrogenated polydecene hydrocarbon oil into a 200 ml glass bottle and put on a hot plate. The sample was next mixed under an overhead mechanical stirrer at a speed of 200 rpm, and heated to 150° C. with temperature control while stirring. After reaching the 150° C., this temperature was maintain while stirring the sample at 300 rpm for 2 hours. Then, heating was discontinued and stirring continued, until the sample was cooled down to around 50-60° C. The resulting opaque paste was poured into a 100 ml glass bottle.

An 18% sample of the PE-g-PDMS opaque paste was then combined into a skin care formulation, Formulation A, along with other ingredients as listed in Table I above.

Comparative Formulation X—No PE-g-PDMS

The control formulation was prepared from the same ingredients as Formulation A, as also listed in Table I above, except no silicone modified polyethylene (PE-g-PDMS) was included.

TABLE II

Skin Lotion Formulations B and Comparative Y

| Trade Name | INCI Name | Comparative Form. Y wt % | Formulation B wt % |
|---|---|---|---|
| Phase I | | | |
| DI Water | Water | q.s. to 100 | q.s. to 100 |
| Glycerin | Glycerin | 2.00 | 2.00 |
| Keltrol CG-SFT (CP Kelco) | Xanthan Gum | 0.70 | 0.70 |
| Phase II | | | |
| Procol CS-20-D (Protameen) | Cetearyl Alcohol (and) Ceteareth 20 | 3.00 | 3.00 |
| RITA GMS (RITA) | Glyceryl Stearate | 2.00 | 2.00 |
| Permethyl 101A (Presperse) | Isohexadecane | 42.00 | |
| 12.5 wt % Polyolefin-g-PDMS smooth gel based on Ex. 5 | | | 48.00 |
| Phase III | | | |
| Neolone PE (Dow) | Phenoxyethaol, Methylisothiazolinone | 0.60 | 0.60 |
| Citric Acid (50% Solution) | Citric Acid | pH = 5.5~6.5 | pH = 5.5~6.5 |

Formulation B—Containing 6% Solids of PE-g-PDMS (Ex5)

The PE-g-PDMS of Example 5 was combined into a skin care formulation, Formulation B, along with other ingredients as listed in Table II above.

Comparative Formulation Y—No PE-g-PDMS

A control formulation was prepared from the same ingredients as Formulation B, as also listed in Table II above, except no silicone modified polyethylene (PE-g-PDMS) was included.

TABLE III

Skin Lotion Formulations C and Comparative Z

| Trade Name | INCI Name | Comparative Form. Z wt % | Formulation C wt % |
|---|---|---|---|
| Phase I | | | |
| DI Water | Water | q.s. to 100 | q.s. to 100 |
| Glycerin | Glycerin | 2.00 | 2.00 |
| Keltrol CG-SFT (CP Kelco) | Xanthan Gum | 0.70 | 0.70 |
| Phase II | | | |
| Procol CS-20-D (Protameen) | Cetearyl Alcohol (and) Ceteareth 20 | 3.00 | 3.00 |
| RITA GMS (RITA) | Glyceryl Stearate | 2.00 | 2.00 |
| Super White Protopet (Sonneborn) | Petrolatum | 5.00 | 5.00 |
| Lilac | C14~22 Alkenes | 40.00 | 15.73 |
| 20.6 wt % of polyolefin-g-PDMS based on Ex. 5, in LILAC | 700MI AMP (XUS38607.00)/NH2-PDMS/ENGAGE 8200 (7.9%/7.9%/4.8%) Lilac (79.4%) | | 24.27 |
| Phase III | | | |
| Neolone PE (Dow) | Phenoxyethaol, Methylisothiazolinone | 0.60 | 0.60 |
| Citric Acid (50% Solution) | Citric Acid | pH = 5.5~6.5 | pH = 5.5~6.5 |

Formulation C—Containing 5% Solids of PE-g-PDMS (Ex6)

The crosslinked PE-g-PDMS of Example 6 was combined into a skin care formulation, Formulation C, along with other ingredients as listed in Table III above.

Comparative Formulation Z—No PE-g-PDMS

A control formulation was prepared from the same ingredients as Formulation C, as also listed in Table III above, except no crosslinked silicone modified polyethylene (PE-g-PDMS) was included.

In-Vivo Skin Sensory Evaluation Method

A trained panelist will clean both forearm and hands by soap. 2 mg/cm$^2$ substance is dispensed on the inside of the forearm. On the other forearm the reference is applied. With the index finger the substance is distributed on the skin. The following parameters (Spreading, Absorption, Tackiness, Oiliness, Waxiness, Smoothness, Softness, and Matte Finish) will be evaluated by the trained panelist (see below description for the evaluation). The rating is on a scale of seven grades: –3, –2, –1, 0, 1, 2, 3. "–3" indicates significantly worse than control; "–2" indicates moderately worse than control; "–1" indicates slightly worse than control; "0" indicates the same sensory performance as the control; "1" indicates slightly better than control; "2" indicates moderately better than control; "3" indicates significantly better than control.

Characteristics of Formulations Evaluated During Experiment

1. Spreading (with index finger): The force to distribute the lotion/cream on the inside of the forearm is compared between substance and reference.
2. Absorption: The absorption of the substance is compared to the reference substance immediately.
3. Tackiness: With the back of the index finger the tackiness of the lotion/cream is tested.
4. Oiliness: The comparison of the film on the skin shows the degree of oiliness.
5. Waxiness: With the index finger the waxiness of the lotion/cream is tested.
6. Smoothness: The surface of the skin of one arm is compared to the other arm by sliding down the arm.
7. Softness: If there is any hardening in the skin this is checked by pressing the fingers onto the skin.
8. Matte Finish: the surface of the skin is checked under light to see if there is a matte appearance or a shine appearance.
9. Smoothness (after rinse-off): the surface of the skin is washed by 0.2 gm of soap for 10 second, rinse off by water for 10 second, and the skin smoothness is checked vs. control.
10. Softness (after rinse-off): the surface of the skin is washed by 0.2 gm of soap for 10 second, rinse off by water for 10 second, and the skin softness is checked vs. control.

Table IV below shows that 6% Polyolefin-g-PDMS (Formulation A) has a better sensory performance compared to the control on absorption, tackiness, oiliness, waxiness, smoothness, softness, matte finish, smoothness (after rinse off), and softness (after rinse off). This indicates that the polyolefin-g-PDMS (a silicone modified polyolefin) can successfully be used as a sensory modifier to improve the aesthetic feel for skin care applications. The after rinse-off smoothness and softness is quite desirable by consumers, and which is challenging to achieve for lotion/cream products. The 6% Polyolefin-g-PDMS (Formulation A) also showed improvement in this aspect compared to the Comparative Formulation X which had no silicon modified polyolefin.

TABLE IV

Sensory evaluation of Formulation A compared to Formulation X

| Parameter | | –3 | –2 | –1 | 0 | 1 | 2 | 3 |
|---|---|---|---|---|---|---|---|---|
| Spreading | Slower | | | | A | | | Faster |
| Absorption | Slower | | | | | A | | Faster |
| Tackiness | Much | | | | | A | | Less |
| Oiliness | Much | | | | | | A | Less |
| Waxiness | Much | | | | | | A | Less |
| Smoothness | Less | | | | | | A | More |
| Softness | Less | | | | | A | | More |
| Matte Finish | Less | | | | | A | | More |
| Smoothness (after rinse off) | Less | | | | | A | | More |
| Softness (after rinse off) | Less | | | | | A | | More |

Reference 0 = Characteristics of Comparative Formulation X
Formulation A (6% Polyolefin-g-PDMS)

Table V shows that Formulation C, the lotion with 6% silicone modified polyolefin has a better sensory performance compared to the Comparative Formulation Z (no polyolefin) on absorption and oiliness. This indicates that the silicone-modified polyolefin can be used as a sensory modifier to improve the aesthetic feel for skin care applications.

TABLE V

Sensory evaluation of Formulation C compared to Formulation Z

| Parameter | | –3 | –2 | –1 | 0 | 1 | 2 | 3 |
|---|---|---|---|---|---|---|---|---|
| Spreading | Slower | | | | A | | | Faster |
| Absorption | Slower | | | | | A | | Faster |
| Tackiness | Much | | | | A | | | Less |
| Oiliness | Much | | | | | A | | Less |
| Waxiness | Much | | | | A | | | Less |
| Smoothness | Less | | | | A | | | More |
| Softness | Less | | | | A | | | More |

Reference 0 = 085273-6 Control
A = 085273-24A (6% Crosslinked Silicone-modified Polyolefin)

In-Vitro Sensory Evaluation

The in-vitro sensory evaluation of skin care lotions was done by friction analysis using an automated tribometer. The friction samples were made by drawing down thin films (~10 grams per square meter) of the skin care lotion on black leneta plastic sheets using an automated coater. The friction measurements were done on a tribometer, where a steel ball (3/8" diameter) is dragged over a coating at a fixed velocity (1 mm/sec) and constant normal load, and the lateral friction force is measured. Multiple measurements were performed for each normal load to conform the reproducibility and the average values are plotted. The normal force (60-90 gm) was specifically chosen to broadly cover the force a person would put on their skin while applying the lotion.

The FIGURE demonstrates the in-vitro sensory test performance of skin care lotions:

Formulation B (Polyolefin-g-PDMS) and Comparative Formulation Y (Control).

The average normal force applied to the sample surface is plotted on the horizontal axis and the corresponding measured average dynamic friction force is plotted on the vertical axis. The higher friction force corresponds to higher drag a person would feel while applying the lotion on their skin. One expects a higher drag force if a lotion is tacky and/or if a lotion is hard to spread. The dynamic friction force captures both these factors and hence, a non-tacky and easy to spread skin care lotion should exhibit lower friction forces.

The plot in the FIGURE shows that the lotion containing the controlled crosslinked polyolefin-g-PDMS of Example 5 exhibits lower friction force than the comparative lotion having no polymer at multiple normal loads. The lower friction force indicates that the controlled crosslinked Polyolefin-g-PDMS sample (Form. B) is less tacky, more smooth/less abrasive, and easier to spread than the control sample (Comp. Form. Y).

What is claimed is:

1. A personal care formulation consisting of:
 (A) a silicone modified polyolefin which is the reaction product of:
  (i) at least one functionalized polyolefin comprising polymerized units derived from one or more olefin monomers selected from $C_2$-$C_{40}$ olefins and having one or more functional groups selected from the group consisting of anhydrides and vinyl silanes of Formula A:

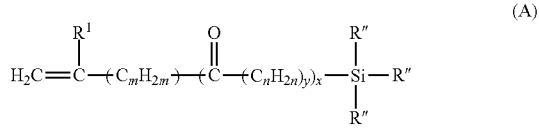

(A)

wherein $R^1$ is a hydrogen atom or methyl group; x and y are 0 or 1, with the proviso that when x is 1, y is 1; m and n are independently an integer from 1 to 12 inclusive; and each R" is, independently, a hydrolyzable organic group selected from the group consisting of an alkoxy group having from 1 to 12 carbon atoms, an aryloxy group, an araloxy group, an aliphatic acyloxy group having from 1 to 12 carbon atoms, an amino group, a substituted amino group, and a lower alkyl group having 1 to 6 carbon atoms inclusive, with the proviso that not more than one of the R" groups is an alkyl; and
  (ii) at least one functionalized silicone polymer comprising polymerized units derived from one or more siloxanes selected from the group consisting of silanol terminated polydimethylsiloxane, mono-aminopropyl terminated polydimethylsiloxane, bis-aminopropyl terminated polydimethylsiloxane, vinyl terminated polydimethylsiloxane, mono-aminopropyl grafted polydimethylsiloxane, bis-aminopropyl grafted polydimethylsiloxane, or vinyl grafted polydimethylsiloxane;
 (B) a carrier; and
 (C) at least one other ingredient selected from the group consisting of emollients, waxes, sensory modifiers, rheology modifiers, humectants, sunscreen actives, bioactives, colorants, particles, emulsifiers, solubilizers, and combinations thereof.

2. The personal care formulation of claim 1, wherein said carrier is selected from the group consisting of: aromatic or aliphatic hydrocarbons, alcohols, aldehydes, ketones, amines, esters, ethers, glycols, glycol ethers, silicone oils, water, and combinations thereof.

3. A method for treating the body which comprises applying the personal care formulation of claim 1 externally to the body.

* * * * *